(12) United States Patent
Furukawa et al.

(10) Patent No.: US 7,018,529 B2
(45) Date of Patent: Mar. 28, 2006

(54) SYSTEM FOR PRODUCING ULTRAPURE WATER

(75) Inventors: Yukihiro Furukawa, Hadano (JP); Masatake Okumura, Shimada (JP)

(73) Assignee: Kurita Water Industries Ltd., Tokyo (JP)

( * ) Notice: Subject to any disclaimer, the term of this patent is extended or adjusted under 35 U.S.C. 154(b) by 83 days.

(21) Appl. No.: 10/792,831

(22) Filed: Mar. 5, 2004

(65) Prior Publication Data
US 2004/0182764 A1    Sep. 23, 2004

(30) Foreign Application Priority Data
Mar. 14, 2003    (JP) .............................. 2003-070330

(51) Int. Cl.
*C02F 1/32* (2006.01)
*C02F 1/42* (2006.01)
*C02F 1/50* (2006.01)

(52) U.S. Cl. ...................... 210/167; 210/202; 210/206; 210/259; 210/266; 210/748; 210/900

(58) Field of Classification Search ................ 210/167, 210/175, 181, 194, 198.1, 201, 202, 206, 210/252, 259, 266, 748, 900, 416.1
See application file for complete search history.

(56) References Cited

U.S. PATENT DOCUMENTS

| | | | | |
|---|---|---|---|---|
| 4,808,287 A | * | 2/1989 | Hark | 210/637 |
| 5,133,854 A | * | 7/1992 | Horvath | 210/121 |
| 5,512,178 A | * | 4/1996 | Dempo | 210/638 |
| 6,416,668 B1 | * | 7/2002 | Al-Samadi | 210/636 |
| 6,475,385 B1 | * | 11/2002 | Boyce et al. | 210/257.2 |
| 6,679,988 B1 | * | 1/2004 | Gsell | 210/181 |
| 2002/0158014 A1 | * | 10/2002 | Yamasaki et al. | 210/631 |
| 2003/0044335 A1 | * | 3/2003 | Jangbarwala | 423/24 |

FOREIGN PATENT DOCUMENTS

| | | |
|---|---|---|
| JP | 6-71269 | 3/1994 |
| JP | 6-312175 | * 11/1994 |
| JP | 2003-71444 | 3/2003 |
| JP | 3480458 | 10/2003 |

* cited by examiner

*Primary Examiner*—Fred G. Prince
(74) *Attorney, Agent, or Firm*—Manabu Kanesaka (57) ABSTRACT

The ultrapure water producing system produces ultrapure water with high purity and remarkably low content of metals even just after restart of operation thereof. Water sent through the pump 3 or 4 into a line 8 flows through a heat exchanger 10, a line 12, a UV oxidation apparatus 20, a line 22, an ion exchange device 30, a line 32 and a membrane filtering device 40 and is treated in each device in this order to be ultrapure water. The devices 10, 20, 30, 40 have bypass lines 11, 21, 31, 41, respectively. In the sterilizing process, bactericide water is fed only to the membrane filtering device 40 via the bypass lines 11, 21 and 31. In the following sterilizing process of the heat exchanger 10 and the UV oxidation apparatus 20, the bactericide water flows the line 41 bypassing around the membrane filtering device 40.

8 Claims, 10 Drawing Sheets

SYSTEM FOR PRODUCING ULTRAPURE WATER

FILED OF THE INVENTION

The present invention relates to a system for producing ultrapure water having an apparatus for producing ultrapure water which is sent to a point of use.

BACKGROUND OF THE INVENTION

Cleaning processes in a semiconductor manufacture field or the like use ultrapure water as cleaning water. The ultrapure water should have a remarkably low content of particles, organic substances or inorganic substances which may cause cleaning troubles. The ultrapure water is usually required to have a water quality having electrical resistivity of higher than 18.2 MΩ·cm and having contents of particles of less than 1 particle/mL, bacteria of less than 1 colony/mL, TOC (Total Organic Carbon) of less than 1 µg/L, silica of less than 1 µL, metals of less than 1 ng/L, and ions of less than 10 ng/mL.

Ultrapure water produced in an ultrapure water producing apparatus is sent to a point of use via sending piping, and residual ultrapure water which is not used in the point of use is recycled to the ultrapure water producing apparatus via returning piping.

Figure 19:
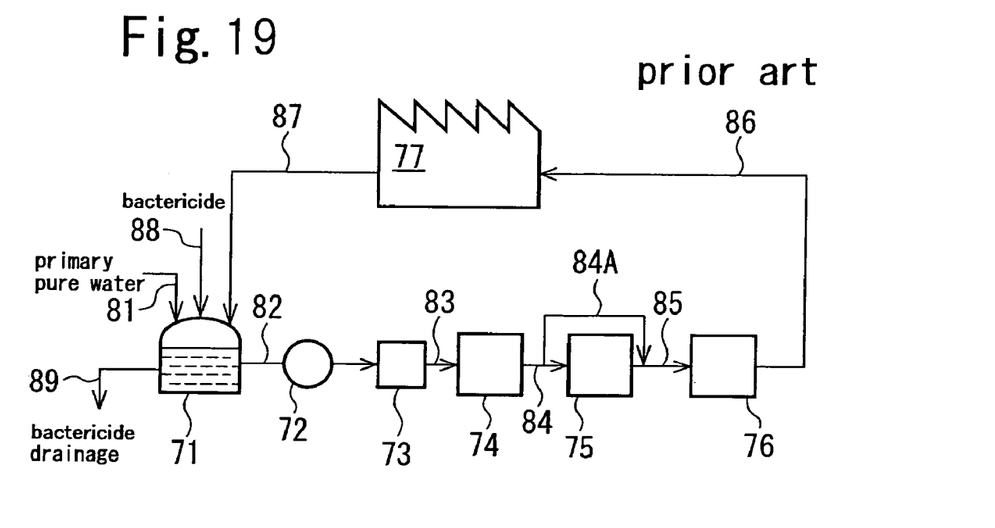
FIG. 19 is a diagram illustrating a conventional system for producing ultrapure water.

FIG. 19 shows a conventional ultrapure water producing system wherein primary pure water stored in a subtank 71 is sent via a pump 72 to a heat exchanger 73 to be heated or cooled, and the water is treated by a UV (ultraviolet) oxidation apparatus 74, an ion exchange device (deionizer) 75, and a UF (ultrafiltration) membrane device 76 to produce ultrapure water. The ultrapure water is sent to a point of use 77 via piping (feeding line) 86. A part of the ultrapure water is used in the point of use 77, and the residual ultrapure water which is not used in the point of use 77 is returned to the subtank 71 via piping (return line) 87.

The primary water is produced by treating raw water such as industrial water, well water and municipal water by a pretreating device such as a coagulation device, and then treating the pretreated water by a first RO (reverse osmosis) device, an ion exchange device (deionizer) containing an anion exchange resin and a cation exchange resin, and a second RO devise in this order.

The point of use 77 includes a cleaning device for cleaning an object such as semiconductors or others, and may further have pipes and nozzles.

The ultrapure water is circulated continuously in the system so as to remove impurities dissolved from constituent materials of pumps, heat exchangers, or pipes of the system and to keep high purity of the ultrapure water. The constituent materials of the pumps, the heat exchanges or some portions of the pipes are usually SUS.

The system for producing ultrapure water is sterilized periodically by supplying water containing bactericide (hereinafter referred to as "bactericide water") to flow through the system in order to reduce the number of bacteria in the ultrapure water fed to the point of use 77 down to less than the number of bacteria required for the level of the above-mentioned water quality requirement. Hydrogen peroxide has been employed as the bactericide, and the system has been sterilized conventionally by the following procedures i) through iii). The ion exchange device (deionizer) 75 is equipped with a bypass line 84A in order not to supply hydrogen peroxide solution therethrough for preventing ion exchange resins from oxidation or deterioration.

i) After the system for producing ultrapure water is stopped running, a concentrated solution of hydrogen peroxide is fed into the subtank 71 via a line (piping) 88 so as to fill the subtank 71 and all the lines with bactericide water containing hydrogen peroxide in a content of about 0.1 to 3%. The bactericide water is circulated through the whole system by the pump 72. Concretely, the bactericide water is circulated through the subtank 71, the line 82, the pump 72, the heat exchanger 73, the line 83, the UV oxidation apparatus 74, the line 84, the bypass line 84A bypassing around the ion exchange device 75, the line 85, the UF membrane device 76, the line 86, the point of use 77, the line 87, and the subtank 71, in this order (hereinafter, this process is referred to as "circulation process"). In this process, the bactericide may be introduced into the subtank 71 through a manhole thereof, or added therein by using an ejector or a pump.

ii) The bactericide water is retained in the system for predetermined period of time after the pump is stopped (herein after, this process is referred to as "steeping process").

iii) The bactericide water in the system is drained out via a drainage line 89 of the subtank 71, and then the subtank 71 is rinsed with water, after that, the system is further rinsed with ultrapure water by using the pump 72 until the bactericide is not detected in the water (hereinafter, this process is referred to as "rinsing process").

After the rinsing process iii), the operation of the system for producing ultrapure water is started again.

Since a density of semiconductor integrated circuits has been increased, ultrapure water for cleaning thereof has been required higher purity, and the ultrapure water system is required to produce ultrapure water with high purity even just at restart of operating the system after its sterilizing treatment.

The inventors have found however that the ultrapure water produced by the system contains metals in a high concentration at reoperation of the system after the sterilizing treatment, and the concentration of metals is kept high for a long period thereafter. Concretely, the ultrapure water sometimes contains 0.1 to 1 ng/L of metals such as Fe, Cr, Ni after the sterilizing treatment, and, in particular, Fe is detected even after 1 week has lapsed from reoperation of the system.

The inventors have investigated causes of the high concentration of metals in the ultrapure water at the reoperation of the system, and found the causes as follows: Metals dissolve into ultrapure water from consistuent materials of pumps, heat exchangers, pipes and so on during operation of the system. Metals also remain in a reserve pump which is out of operation. These metals are oxidized by hydrogen peroxide and dissolve into the water. The dissolved metals form particles of metal hydroxides. The particles thus formed are captured by a membrane in a membrane separation device arranged at the last stage of the ultrapure water producing apparatus. The captured particles re-dissolve into the ultrapure water after hydrogen oxide is drained out of the system during a rinsing process.

SUMMARY OF THE INVENTION

It is an object of the present invention to provide an ultrapure water producing system which produces ultrapure water with high purity and a stable water quality and remarkably low content of metals even just after restart of operation thereof after sterilizing treatment in the system.

An ultrapure water producing system of the present invention has a subtank for storing primary water (deionized water); an ultrapure water producing apparatus for treating primary water to produce ultrapure water, the ultrapure water producing apparatus having at least an ultraviolet oxidization device, an ion exchange device (a deionizer), and a membrane separation device which are arranged in this order; a supplying line for supplying ultrapure water produced by the ultrapure water producing apparatus to a point of use; and a return line for returning residual ultrapure water passed through the point of use without being used therein to the subtank. The system has means which makes bactericide water flow through the membrane separation apparatus while bypassing the devices arranged at the upstream side of the membrane separation device. The system also has means which makes the bactericide water flow through the device arranged at the upstream side of the ion exchange device (deionizer), and makes the bactericide water flowing out of the upstream side device bypass the ion exchange device (deionizer) and the membrane separation device.

In the system for producing ultrapure water of the invention, the cleaning water (bactericide water) which cleaned the devices arranged at the upstream side of the ion exchange device (deionizer) bypasses the membrane device. Accordingly, particles generated by cleaning water at the upstream side devices are not captured by the membrane device. As a result thereof, at a restart of operation of the system, the rise in an ion concentration of metals which redissolve into the water from the particles is prevented.

The ultrapure water producing system of the present invention may have means for feeding bactericide to water stored in the subtank to prepare bactericide water whereby the bactericide water in the subtank is sent therefrom for cleaning the devices; and means for substituting bactericide water in the subtank for primary water.

The ultrapure water producing system of the present invention may have a first pump for pumping and sending the primary water from the subtank (Hereinafter, it is referred to as "a subpump" as the case may be); a second pump (a sterilizing-purpose pump) which is used only for pumping and sending the bactericide water from the subtank; and means for exhausting water out of the system through the sending side of the first pump out of the system. The system may further have a loop line for returning water pumped by the second pump without passing through any of the devices, and the loop line may be provided with adding means for adding bactericide thereinto.

The ultrapure water producing system may have a heat exchanger and other devices arranged at the upstream side of the ultraviolet oxidation device.

According to an aspect of the invention, each of the devices is respectively provided with a bypass line which bypasses only each device.

According to another aspect of the invention, the ultrapure water producing system has a first bypass line bypassing only the membrane separation device; a second bypass line bypassing only the ion exchange device (the deionizer); and a third bypass line bypassing a group consisting of the ion exchange device (the deionizer) and the devices at the upstream side of the ion exchange device (the deionizer) as a whole.

DETAILED DESCRIPTION OF THE PREFERRED EMBODIMENTS

Hereinafter, preferred embodiments of a system for producing ultrapure water of the present invention will be described in detail with reference to attached drawings.

Figure 1:
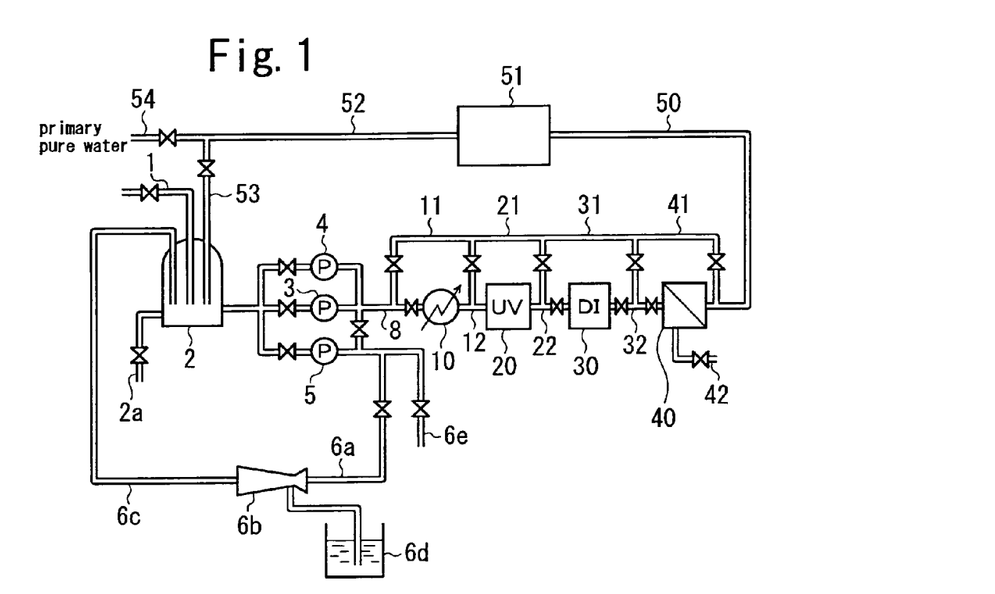
FIG. 1 is a diagram illustrating an preferred embodiment of a system for producing ultrapure water of the present invention.

FIG. 1 is a diagram illustrating an embodiment of a system for producing ultrapure water of the present invention.

Primary pure water (deionized water) is supplied into a subtank 2 through a line (piping) 1 to be stored therein. The water stored in the subtank 2 is sent through a pump 3. A pump 4 is a reserve one. The pumps 3 and 4 are arranged in parallel. A sterilizing pump 5 which is used only for pumping and sending bactericide water from the subtank 2 is further installed in parallel with the pumps 3 and 4.

A blow line 6e branches from the sending line of the pumps 3, 4 and 5.

The water sent by the pump 3 or 4 through a line 8 can flow through a heat exchanger 10, a line 12, a UV oxidation apparatus 20 such as a low-pressure ultraviolet oxidation apparatus, a line 22, an ion exchange device (deionizer, DI. deionization) 30, a line 32 and a membrane filtering device 40 and is treated in each device in this order to be ultrapure water. The ultrapure water is sent to a point of use 51 via a supply line 50, and the residual water which is not used in the point of use 51 is returned via return lines 52 and 53. The membrane filtering device 40 has a brine draining line 42. Each of the lines 8, 12, 22, 32, 50, 52, 53 and 54 has a valve. In FIG. 1, only main valves are shown. Similarly lines 2a, 6a, 6c, 6e, 11, 21, 31, 41, etc. which will be mentioned later have valves.

The system is provided with a device for adding bactericide into the water in the subtank 2 in order to feed bactericide water to each of the aforementioned devices 10, 20, 30, 40. The bactericide adding device has lines 6a, 6c which branch from the sending line of the sterilizing pump 5 and return to the subtank 2, an ejector 6b which receives the water from the line 6a and sends the water into the line 6c, and a bactericide tank 6d for feeding hydrogen peroxide solution as bactericide water to the ejector 6b. The bactericide tank 6d is utilized for storing and carrying hydrogen peroxide solution in the sterilizing process of the system.

A blow line 6e which is used for replacing the water in the sterilizing pump 5 with primary pure water is connected to the sending line of the sterilizing pump 5. The subtank 2 has a blow line 2a which is used for replacing the water therein with primary pure water.

The aforementioned devices 10, 20, 30, 40 have bypass lines 11, 21, 31, 41, respectively. Each of the bypass lines 11, 21, 31, 41 bypasses around each of the devices 10, 20, 30, 40, respectively. The bypass line 11 for the heat exchanger 10 connects the lines 8 and 12. The bypass line 21 for the UV oxidation apparatus 20 connects the lines 12 and 22. The bypass line 31 for the ion exchange device 30 connects the lines 22 and 32. The bypass line 41 for the membrane filtering device 40 connects the line 32 and the supply line 50.

A blow line 54 used in the rinsing process branches from the return line 52.

Hereinafter, the operation of the aforementioned system for producing ultrapure water will be described.

I. Production of Ultrapure Water

Figure 2:
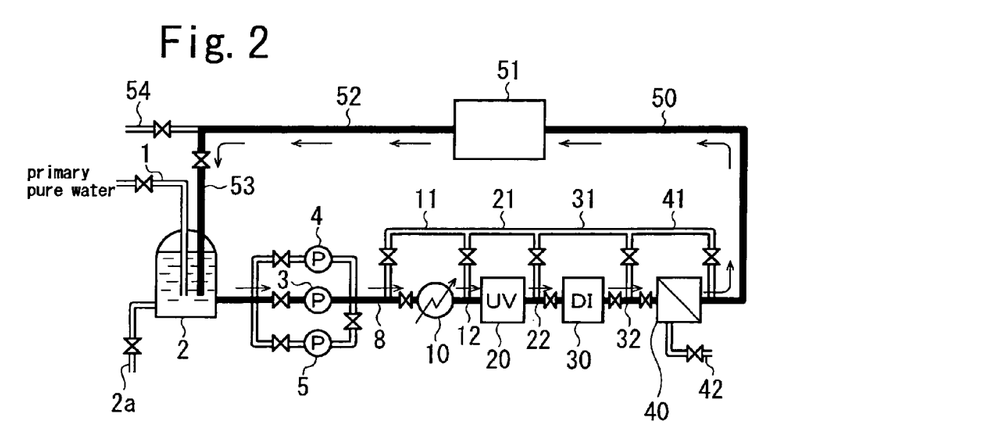
FIG. 2 is a flow diagram illustrating the system of FIG. 1 in the ultrapure water producing operation.

When the system for producing ultrapure water is in the ultrapure water producing operation, as shown in FIG. 2, primary pure water (deionized water) in the subtank 2 flows through the pump 3, the heat exchanger 10, the UV oxidation apparatus 20, the ion exchange device 30, the membrane filtering device 40, the supply line 50, the point of use 51, and the return lines 52 and 53, in this order. In this operation, the pump 5 does not work and the water does not flow through the bypass lines 11, 21, 31 and 41.

II. Sterilization

Sterilization is done in the following manner:

(i) Feed of Bactericide to the Subtank

Firstly, water is drained from the subtank 2 so as to reduce the water level in the subtank 2 to about ⅓ to ¼. In this drainage, the pumps 3 and 4 are operated to drain the primary pure water through both the aforementioned primary pure water blow line 6e and the blow line 54 which branches from the return line, so that the water containing heavy metals which has remained in the reserve pump, etc. is drained out of the system.

Figure 3:
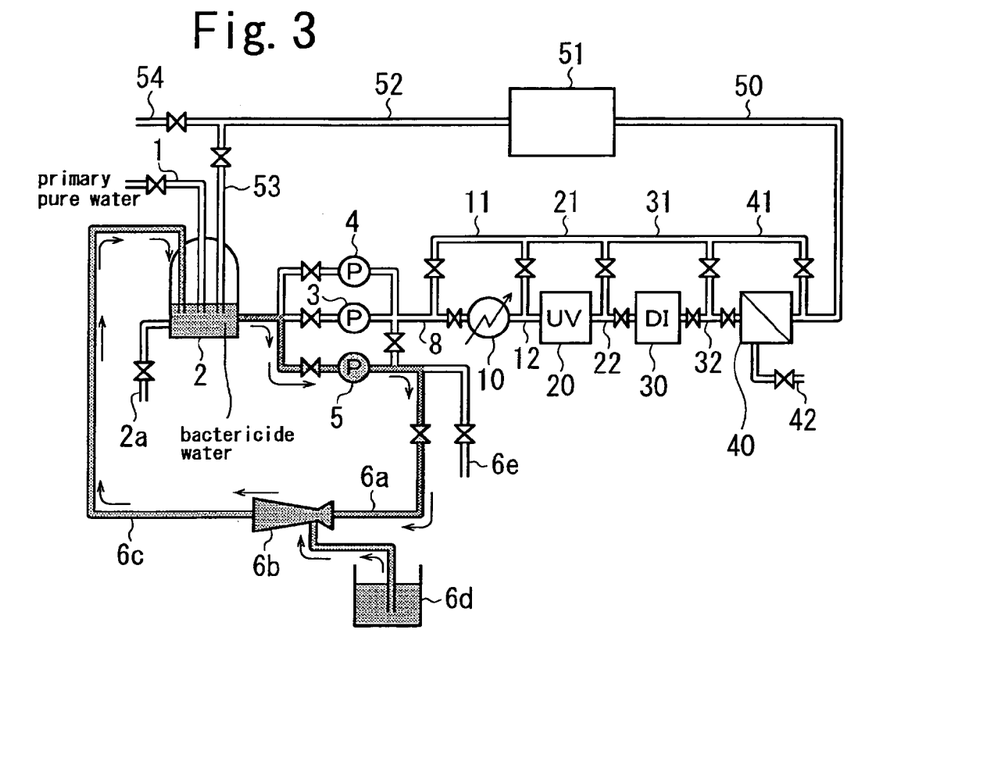
FIG. 3 is a flow diagram illustrating the system of FIG. 1 in the first step of a sterilizing process.

Secondly, as shown in FIG. 3 (the first step) the sterilizing pump 5 is operated to feed the water into the lines 6a and 6c, and hydrogen peroxide solution in the bactericide tank 6d is added into the primary pure water in the subtank 2 by the ejector 6b. After the content of hydrogen peroxide in the water in the subtank 2 and the lines reaches the predetermined value (for example, 0.1 to 5%), the sterilizing pump 5 is stopped running.

The bactericide water stored in the subtank 2 in this process does not contain any metal ions.

(ii) Sterilization of the Membrane Filtering Device 40

Figure 4:
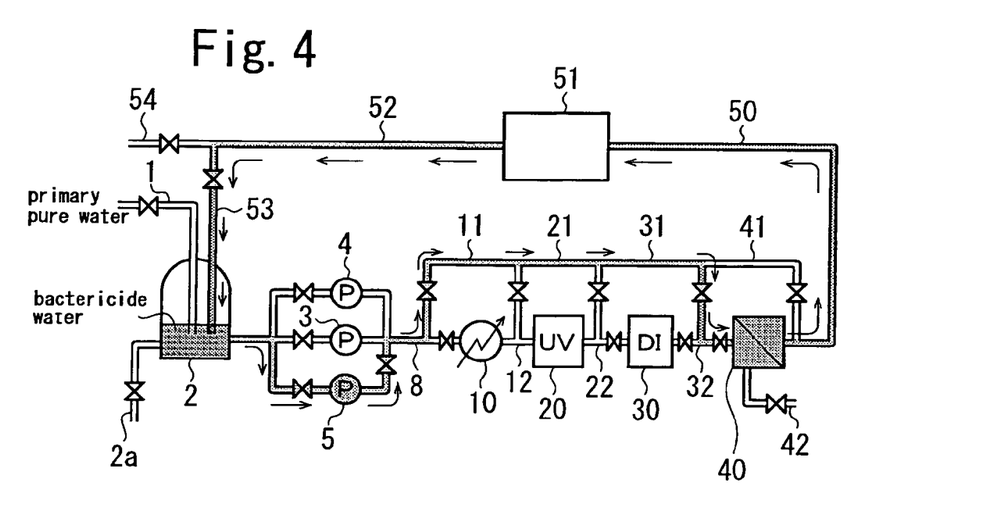
FIG. 4 is a flow diagram illustrating the system of FIG. 1 in the second step of a sterilizing process.

The membrane filtering device 40 is first sterilized by feeding the bactericide water therethrough. As shown in FIG. 4 (the second step), the bactericide water in the subtank 2 is taken out and flows through the sterilizing pump 5, the line 8, the bypass lines 11, 21, 31, the membrane filtering device 40 and the lines 50, 52, 53 in this order to sterilize the membrane filtering device 40. The bactericide water returning through the line 53 is collected into the subtank 2. The feed of the bactericide water is kept for 10 to 15 minutes after hydrogen peroxide is detected in the water in the downstream line of the membrane filtering device 40.

In this process for sterilizing the membrane filtering device 40, since the bactericide water which does not contain any metals in the subtank 2 bypasses the devices 10, 20, 30 and flows into the membrane filtering device 40 directly, the membrane filtering device 40 does not catch any metal oxide particles. The ion exchange resin is not deteriorated because the bactericide water (hydrogen peroxide solution) does not flow through the ion exchange device 30.

(iii) Sterilization of the Heat Exchanger 10 and the UV Oxidation Apparatus 20

Figure 5:
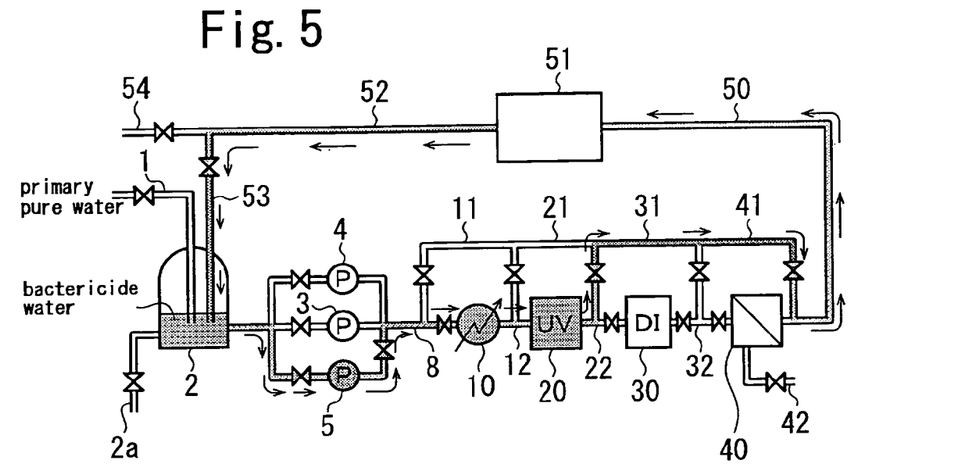
FIG. 5 is a flow diagram illustrating the system of FIG. 1 in the third step of a sterilizing process.

As shown in FIG. 5 (the third step), the heat exchanger 10 and the UV oxidation apparatus 20 are sterilized secondly by feeding the bactericide water in the subtank 2 through the line 8, the heat exchanger 10, the UV oxidation apparatus 20, the bypass lines 31, 41 and the lines 50, 52, 53 in this order. The feed of the bactericide water in this process is kept until hydrogen peroxide is detected in the water flowing into the subtank 2 through the line 53.

In this process, since the bactericide water flowing through the heat exchanger 10 and the UV oxidation apparatus 20 does not flow into the membrane filtering device 40, the membrane filtering device 40 is not contaminated by the particles. The ion exchange resin is not deteriorated because the bactericide water (hydrogen peroxide solution) does not flow through the ion exchange device 30.

iv) Steeping by the Bactericide Water and Replacement the Bactericide Water in the Subtank 2 with Primary Pure Water When hydrogen peroxide is detected in the water returning through the line 53 in the above process (iii), the sterilizing pump 5 is stopped running. This state is kept for about 1 to 3 hours, for example, about 2 hours (steeping process). In this steeping process, each of the devices 10, 20, 40 and the lines are filled with the bactericide water, so that the sterilization of each member is carried out.

Figure 6:
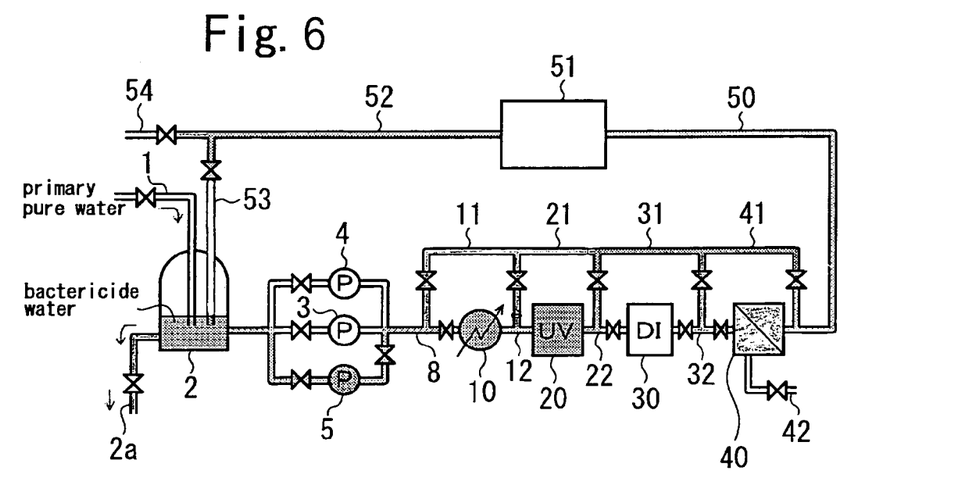
FIG. 6 is a flow diagram illustrating the system of FIG. 1 in the fourth step of a sterilizing process.

On the other hand, during the steeping process, the water in the subtank 2 is replaced with primary pure water. In this replacing process, the bactericide water in the subtank 2 is drained out completely through the blow line 2a, as shown in FIG. 6 (the fourth step) and then primary pure water is supplied into the subtank 2 through the line 1 to rinse the subtank 2. The rinsing treatment by primary pure water is repeated three times. In this rinsing process, primary pure water is enough to be supplied to the water level as high as that of the hydrogen peroxide solution fed at the beginning, and need not be supplied to the top of the subtank 2.

Figure 7:
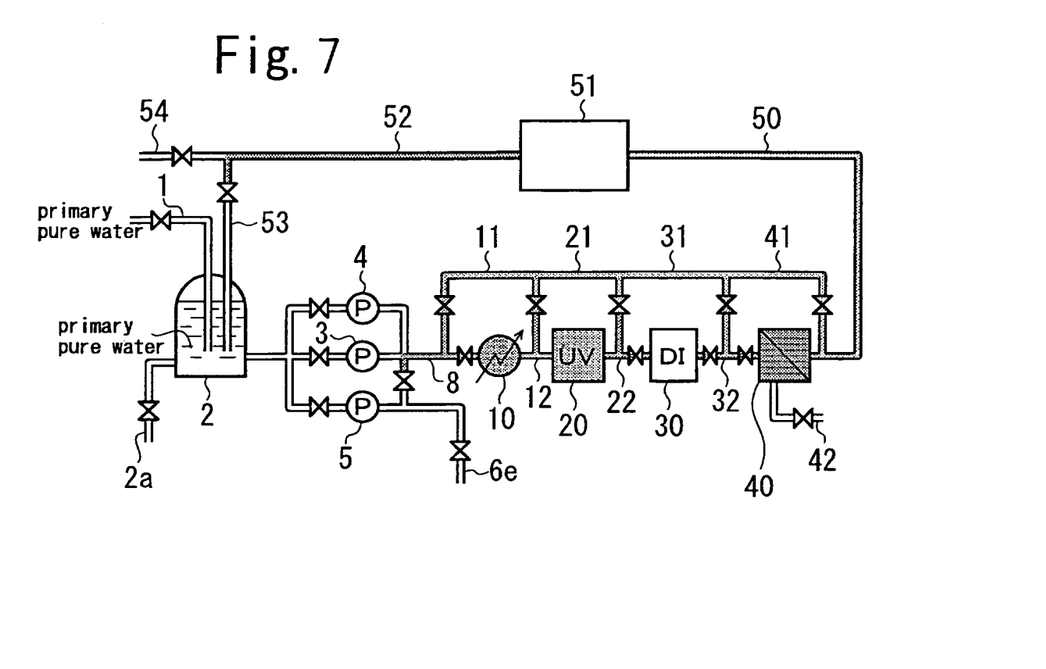
FIG. 7 is a flow diagram illustrating the system of FIG. 1 in the fifth step of a sterilizing process.

After three-times rinsing treatment, the subtank 2 is filled with primary pure water. And then the sterilizing pump 5 is rinsed by feeding a predetermined amount of primary pure water through the blow line 6e while primary pure water is supplied to the subtank 2 through the line 1. FIG. 7 (the fifth step) shows the state after the pump 5 is rinsed. It is preferable that the pumps 3, 4 are rinsed in the same manner as the pump 5.

(v) Rinsing Treatment of the Bypass Lines 11, 21, 31, 41

Figure 8:
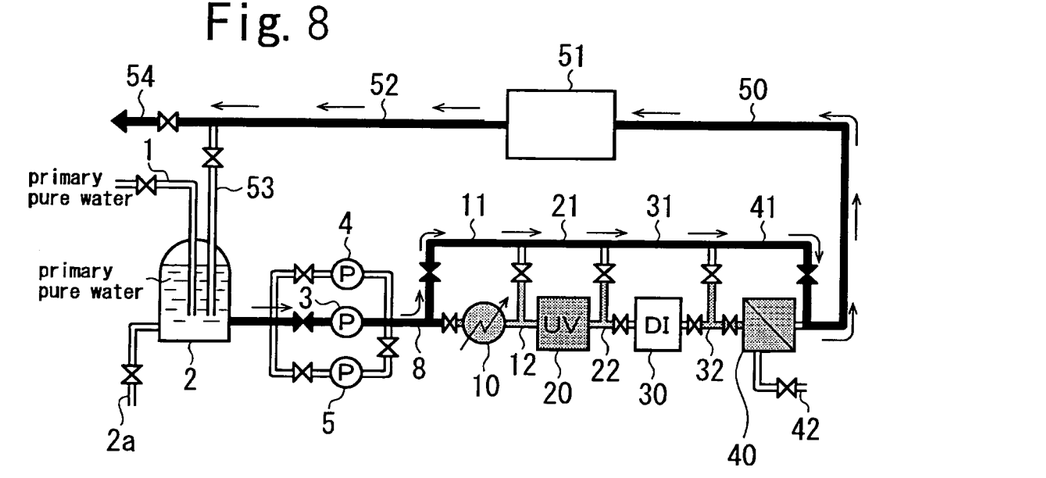
FIG. 8 is a flow diagram illustrating the system of FIG. 1 in the first step of a rinsing process.

As shown in FIG. 8 (the first step), the bypass lines 11, 21, 31, 41 are rinsed by feeding primary pure water in the subtank 2 through the pump 3, the line 8, the bypass lines 11, 21, 31, 41 and lines 50, 52, 54 in this order while primary pure water is supplied to the subtank 2 through the line 1. The water after the rinsing treatment does not return to the subtank 2, but is drained out through the blow line 54. The feed of water is kept until hydrogen peroxide is not detected in the drained water flowing out through the blow line 54 or at the outlet of the membrane filtering device 40.

(vi) Rinsing Treatment of the Heat Exchanger 10 and the UV Oxidation Apparatus 20

Figure 9:
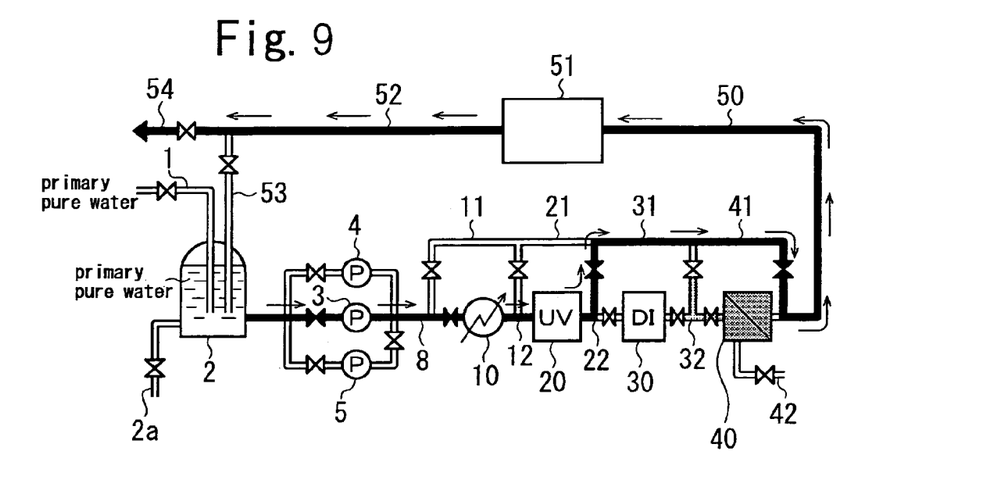
FIG. 9 is a flow diagram illustrating the system of FIG. 1 in the second step of a rinsing process.

As shown in FIG. 9 (the second step), the heat exchanger 10 and the UV oxidation apparatus 20 are rinsed by feeding primary pure water in the subtank 2 through the pump 3, the line 8, the heat exchanger 10, the UV oxidation apparatus 20, the bypass lines 31, 41 and the lines 50, 52, 54 in this order while primary pure water is supplied to the subtank 2 through the line 1. The water after the rinsing treatment does not return to the subtank 2, but is drained out through the blow line 54. The feed of water is kept until hydrogen peroxide is not detected in the drained water flowing out through the blow line 54 or at the outlet of the membrane filtering device 40.

(vii) Feed of Primary Pure Water Into the Ion Exchange Device 30

Figure 10:
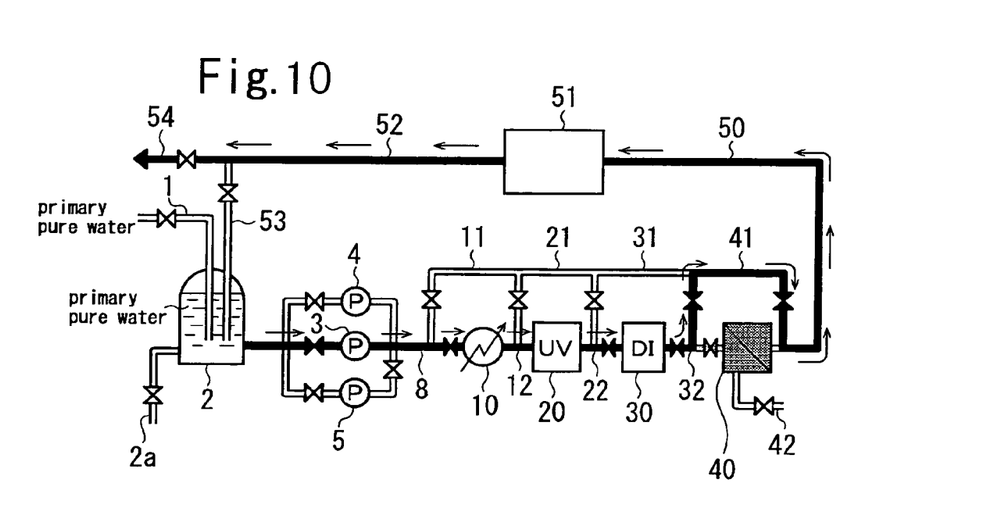
FIG. 10 is a flow diagram illustrating the system of FIG. 1 in the third step of a rinsing process.

As shown in FIG. 10 (the third step), primary pure water in the subtank 2 is fed to flow through the pump 3, the line 8, the heat exchanger 10, the UV oxidation apparatus 20, the ion exchange device 30, the bypass lines 41 and the lines 50, 52, 54 in this order while being supplied to the subtank 2 through the line 1.

The feed of water is kept until hydrogen peroxide is not detected in the drained water flowing out through the blow line 54 or at the outlet of the membrane filtering device 40.

(viii) Rinsing Treatment of the Membrane Filtering Device 40

Figure 11:
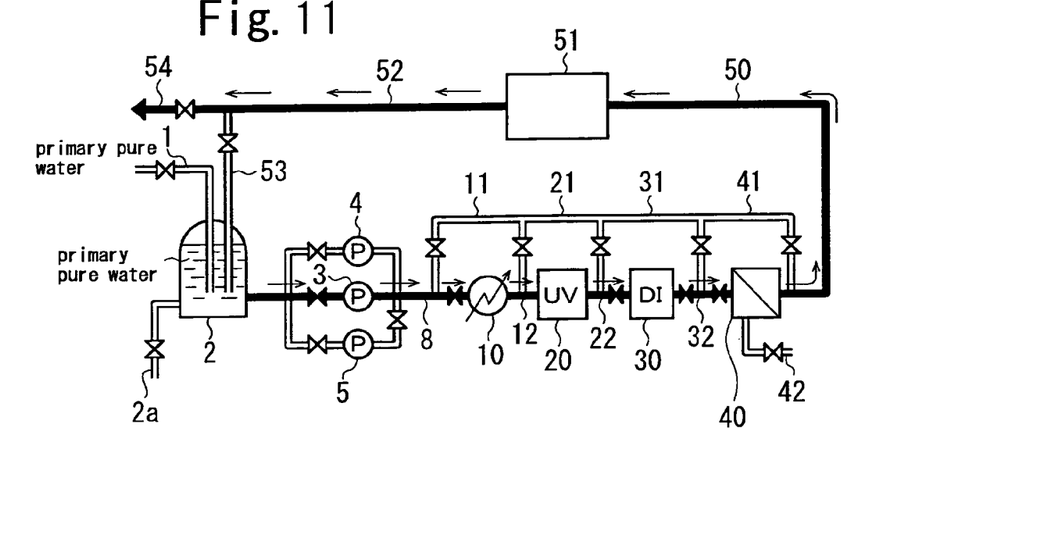
FIG. 11 is a flow diagram illustrating the system of FIG. 1 in the fourth step of a rinsing process.

Finally, as shown in FIG. 11 (the fourth step), primary pure water in the subtank 2 is fed to flow through the line 8, the devices 10, 20, 30 and the membrane filtering device 40 and then drained through the lines 50, 52, 54. The feed of water is kept until hydrogen peroxide is not detected in the drained water flowing out through the line 54.

When hydrogen peroxide is not detected in the drained water from the line 54, the valve of the blow line 54 is closed and the valve of the return line 53 is opened so that the system returns to the usual operation as shown in FIG. 2. Since the membrane filtering device 40 have not captured any particles of metal hydroxide, the system can produce ultrapure water with high purity even just after return to the usual operation thereof.

Figure 12:
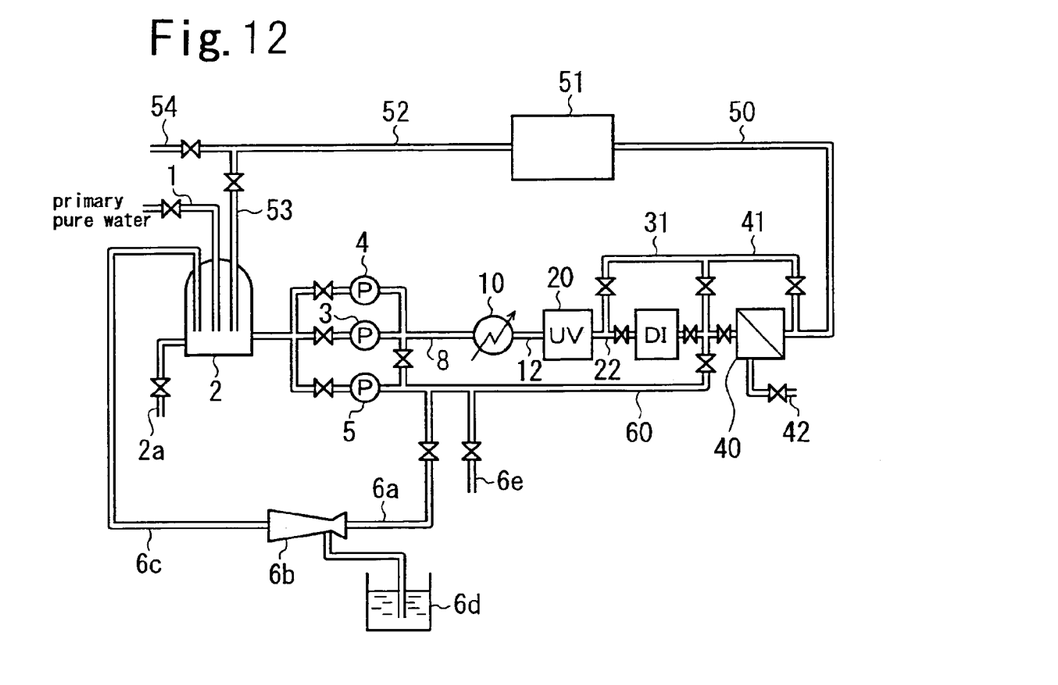
FIG. 12 is a diagram illustrating another preferred embodiment of a system for producing ultrapure water of the present invention.

Although each of the devices 10, 20, 30, 40 has the bypass lines 11, 21, 31, 41, respectively, in the aforementioned embodiment, the system may have a bypass line 60 bypassing around the heat exchanger 10, the UV oxidation apparatus 20 and the ion exchange device 30 which are arranged at the upstream side of the membrane filtering device 40, as shown in FIG. 12, where the system does not have the bypass lines 11, 21 which bypassing around the devices 10, 20, respectively, but has the bypass lines 31, 41.

In the embodiment of FIG. 12, the usual operation of the system is carried out in the same manner as shown in FIG. 2, and the introduction of bactericide in the subtank 2 is carried out in the same manner as shown in FIG. 3. The sterilizing and rinsing process in the system are carried out in a manner as shown in FIGS. 13 through 18.

Figure 13:
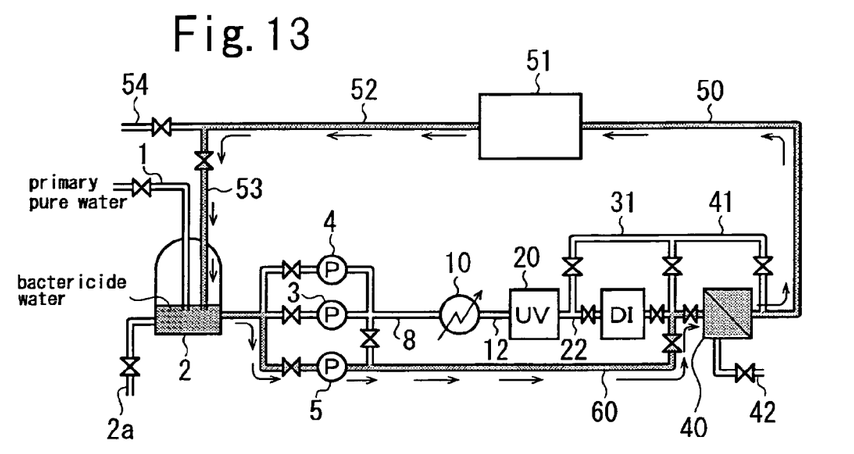
FIG. 13 is a flow diagram of the system of FIG. 12 in the first step of a sterilizing process.

In the sterilizing process, bactericide is added into primary pure water in the subtank 2 and then the pure bactericide water in the subtank 2 is fed from the pump 5 through the bypass line 60, the membrane filtering device 40 and the lines 50, 52, 53 in this order firstly as shown in FIG. 13 (the first step).

Figure 14:
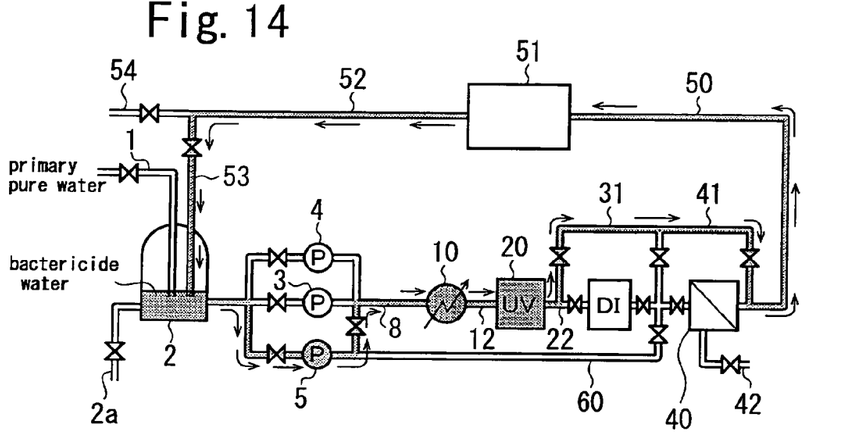
FIG. 14 is a flow diagram of the system of FIG. 12 in the second step of a sterilizing process.

Secondly, the bactericide water in the subtank 2 is fed to flow through the heat exchanger 10, the UV oxidation apparatus 20, the bypass lines 31, 41 and the lines 50, 52, 53 in this order as shown in FIG. 14 (the second step).

Then, the steeping process is carried out for 2 hours in the same manner as shown in FIG. 7. On the other hand, the bactericide water in the subtank 2 is replaced with primary pure water during the steeping process. After that, the sterilizing pump 5 is rinsed by the primary pure water.

Figure 15:
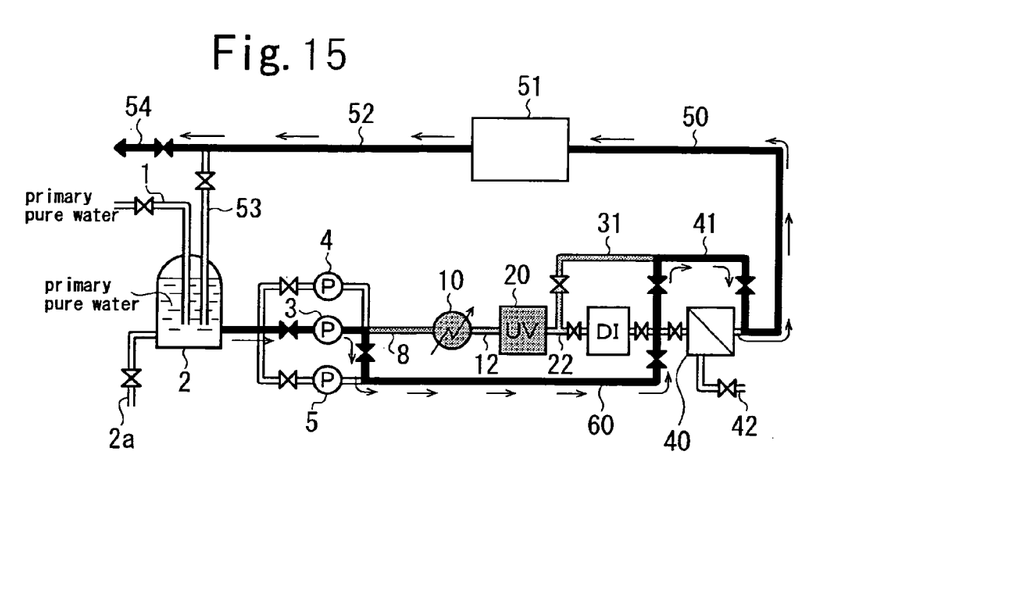
FIG. 15 is a flow diagram of the system of FIG. 12 in the first step of a rinsing process.

Secondly, in the rinsing process, the water in the subtank 2 is fed to flow through the pump 3, the bypass lines 60, 41 and the lines 50, 52, 54 in this order to rinse the bypass lines 60 and 41 while primary pure water is supplied into the subtank 2, as shown in FIG. 15 (the first step).

Figure 16:
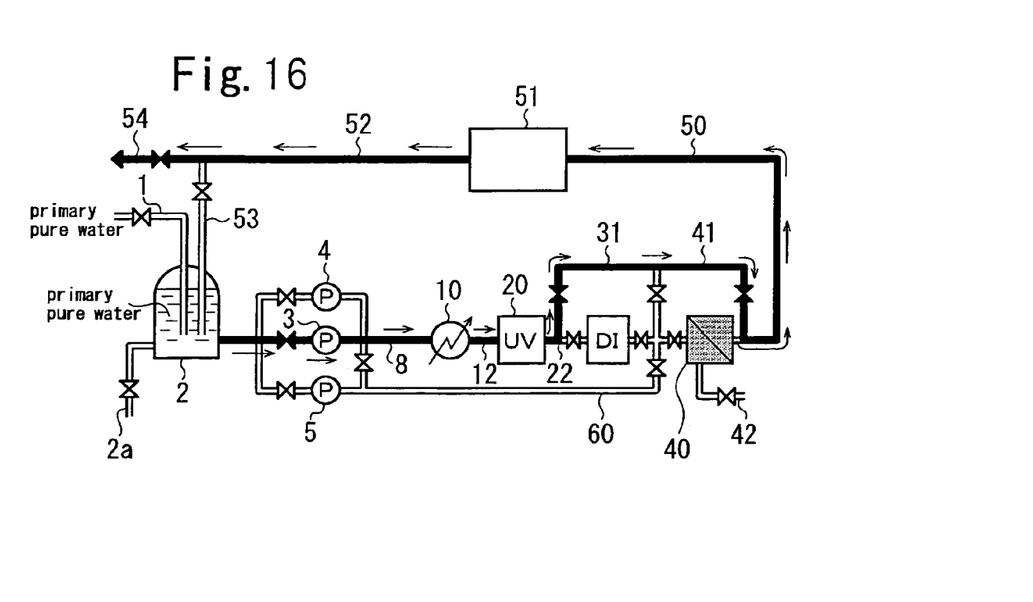
FIG. 16 is a flow diagram of the system of FIG. 12 in the second step of a rinsing process.

Thirdly, the water in the subtank 2 is fed to flow through the pump 3, the heat exchanger 10, the UV oxidation apparatus 20, the bypass lines 31, 41 and the lines 50, 52, 54 in this order to rinse the heat exchanger 10 and the UV oxidation apparatus 20, as shown in FIG. 16 (the second step).

Figure 17:
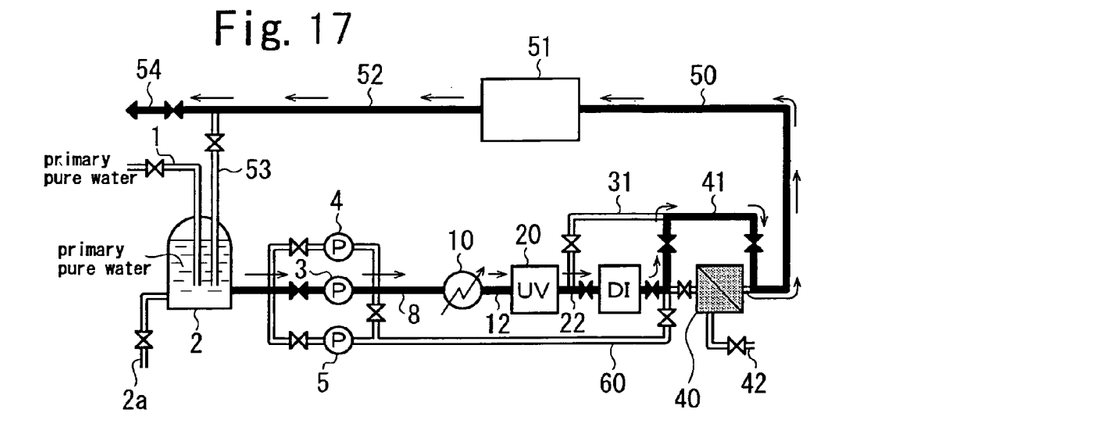
FIG. 17 is a flow diagram of the system of FIG. 12 in the third step of a rinsing process.

Fourthly, the water in the subtank 2 is fed to flow through the pump 3, the devices 10, 20, 30, the bypass line 41 and the lines 50, 52, 54 in this order to be certain that hydrogen peroxide is not detected in the water flowing out through the line 54 or at the outlet of the membrane filtering device 40, as shown in FIG. 17 (the third step).

Figure 18:
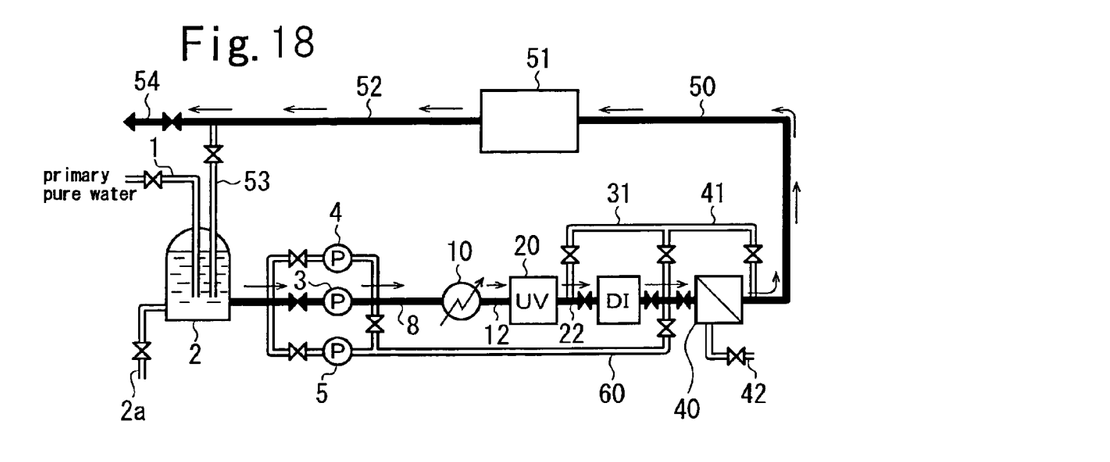
FIG. 18 is a flow diagram of the system of FIG. 12 in the fourth step of a rinsing process.

Finally, as shown in FIG. 18 (the fourth step) the water in the subtank 2 is fed to flow through the devices 10, 20, 30, 40 and the lines 30, 52, 54 in this order. When hydrogen peroxide is not detected in the water flowing out through the blow line 51, the usual operation is resumed.

Although it takes 7 to 14 days after the sterilizing process to return the purity of ultrapure water to the level before the usual operation is discontinued according to the conventional method, it takes 0.25 to 1 day after the sterilizing process to return the purity of ultrapure water to the level before the usual operation is discontinued according to the present invention.

Each of the aforementioned embodiments is just a example of the present invention, and the system for producing ultrapure water of the present invention may have other constituents than the embodiments. For example, the system of the present invention may have other devices at the upstream side of the ion exchange device. The system of the present invention may have any membrane filtering device, such as a UF membrane device, a precision filtering membrane device, a reverse osmosis membrane device, or a device composed of two or more of these membrane devices.

In case that the system has a membrane deaeration device at the upstream or downstream side of the ion exchange device, the system also has a bypass line bypassing around the membrane deaeration device in the same manner as that of the membrane filtering device. In the sterilizing process of the membrane deaeration device, problems occur due to the membrane filtration of the membrane filtering device as mentioned above. The sterilizing process of the membrane deaeration device may be carried out in the same manner as the aforementioned sterilizing process (ii) of the membrane filtering device 40. The sterilization of the membrane filtering device and the membrane deaeration device may be carried out at the same time in the process (ii). In this case, the bactericide water is fed to flow through the membrane filtering device 40 and the membrane deaeration device while bypassing around other devices to sterilize the membrane deaeration device. On the other hand, the membrane filtering device and membrane deaeration device may be sterilized separately or individually in the process (ii). In this case, the membrane deaeration device may be sterilized before or after the membrane filtering device. The processes following the sterilizing process of the membrane filtering device and the membrane deaeration device may carried out in the same manner as mentioned above.

The system of the present invention may have any ion exchange device, such as a cartridge polisher (non-regeneration ion exchange resin device) or a electric deionized water producing device.

As described above, according to the present invention, an ultrapure water producing system which produces ultrapure water with high purity and remarkably low content of metals even just after restart of operation thereof can be provided.

What is claimed is:

1. An ultrapure water producing system comprising:
   a subtank for storing primary water;
   an ultrapure water producing apparatus for treating primary water to produce ultrapure water comprising at least an ultraviolet oxidization device, an ion exchange device, and a membrane separation device which are arranged in this order;
   a supplying line for supplying ultrapure water produced by the ultrapure water producing apparatus to a point of use;
   a return line for returning residual ultrapure water passed through the point of use without being used therein to said subtank;
   means for passing bactericide water through said membrane separation device with bypassing the devices arranged at the upstream side of said membrane separation device;
   means for passing the bactericide water through said device arranged at the upstream side of said ion exchange device, and making the bactericide water flowing out of said device bypass said ion exchange device and said membrane separation device;
   means for feeding bactericide to water stored in said subtank to prepare the bactericide water whereby the bactericide water in the subtank is sent therefrom for cleaning the devices; and
   means for substituting the bactericide water in the subtank for primary water.

2. An ultrapure water producing system as claimed in claim 1, wherein said system has a first pump for pumping and sending primary water from the subtank and a second pump which is used only for pumping and sending the bactericide water from the subtank.

3. An ultrapure water producing system as claimed in claim 2, wherein said system has means for exhausting water from the downstream side of said first pump out of the system.

4. An ultrapure water producing system as claimed in claim 2, wherein said system has a loop line for returning water pumped by said second pump without passing through any of said devices, and the loop line is provided with adding means for adding the bactericide thereinto.

5. An ultrapure water producing system as claimed in claim 1, wherein said ultrapure water producing apparatus further comprises a heat exchanger arranged at the upstream side of said ultraviolet oxidation device.

6. An ultrapure water producing system as claimed in claim 5, wherein each of said devices is respectively provided with a bypass line which bypasses only each device.

7. An ultrapure water producing system comprising:
   a subtank for storing primary water;
   an ultrapure water producing apparatus for treating primary water to produce ultrapure water comprising at least an ultraviolet oxidization device, an ion exchange device, and a membrane separation device which are arranged in this order, wherein each of said devices is respectively provided with a bypass line which bypasses only each device;
   a supplying line for supplying ultrapure water produced by the ultrapure water producing apparatus to a point of use;
   a return line for returning residual ultrapure water passed through the point of use without being used therein to said subtank;
   means for passing bactericide water through said membrane separation device with bypassing the devices arranged at the upstream side of said membrane separation device; and
   means for passing the bactericide water through said device arranged at the upstream side of said ion exchange device, and making the bactericide water flowing out of said device bypass said ion exchange device and said membrane separation device.

8. An ultrapure water producing system comprising:
   a subtank for storing primary water;
   an ultrapure water producing apparatus for treating primary water to produce ultrapure water comprising at least an ultraviolet oxidization device, an ion exchange device, and a membrane separation device which are arranged in this order;
   a supplying line for supplying ultrapure water produced by the ultrapure water producing apparatus to a point of use;
   a return line for returning residual ultrapure water passed through the point of use without being used therein to said subtank;
   means for passing bactericide water through said membrane separation device with bypassing the devices arranged at the upstream side of said membrane separation device;
   means for passing the bactericide water through said device arranged at the upstream side of said ion exchange device, and making the bactericide water flowing out of said device bypass said ion exchange device and said membrane separation device;
   a first bypass line bypassing only said membrane separation device;
   a second bypass line bypassing only said ion exchange device; and
   a third bypass line bypassing a group consisting of said ion exchange device and said device at the upstream side of the ion exchange device.

* * * * *